United States Patent [19]

Paust et al.

[11] Patent Number: 5,489,694
[45] Date of Patent: Feb. 6, 1996

[54] PREPARATION OF R/S-γ-LIPOIC ACID OR R/S-α-LIPOIC ACID

[75] Inventors: Joachim Paust, Neuhofen; Peter Eckes, Otterstadt; Wolfgang Siegel, Mannheim; Friedhelm Balkenhohl, Limburgerhof; Walter Dobler, Heidelberg; Michael Hüllmann, Heppenheim, all of Germany

[73] Assignee: BASF Aktiengesellschaft, Ludwigshafen, Germany

[21] Appl. No.: 279,418

[22] Filed: Jul. 25, 1994

Related U.S. Application Data

[62] Division of Ser. No. 113,089, Aug. 30, 1993, Pat. No. 5,380,920.

[30] Foreign Application Priority Data

Sep. 8, 1992 [DE] Germany ............... 42 29 914.4
Jun. 18, 1993 [DE] Germany ............... 43 20 230.6

[51] Int. Cl.⁶ .................... C07D 339/04; C07C 53/126
[52] U.S. Cl. ............................. 549/39; 562/512
[58] Field of Search ..................... 562/512; 549/39

[56] References Cited

U.S. PATENT DOCUMENTS 2,993,056  7/1961  Segre et al. ................ 260/343

OTHER PUBLICATIONS

Yadav et al., *J. Sci Ind Res*, 49, pp. 400–409 (1990).
CA 63: 16355g (1965).

*Primary Examiner*—Paul F. Shaver
*Assistant Examiner*—Barbara S. Frazier
*Attorney, Agent, or Firm*—Keil & Weinkauf

[57] ABSTRACT

A process for preparing R/S-γ-lipoic acid of the formula I or R/S-α-lipoic acid of the formula II

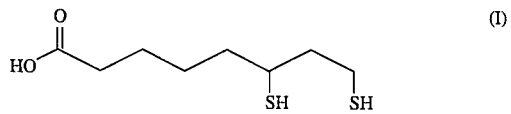

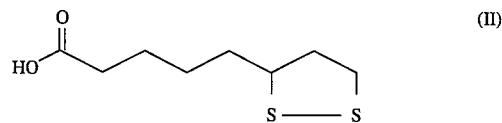

is disclosed.

3 Claims, No Drawings

PREPARATION OF R/S-γ-LIPOIC ACID OR R/S-α-LIPOIC ACID

This is a divisional of application Ser. NO. 08/113,089, filed Aug. 30, 1993, now U.S. Pat. No. 5,380,920.

The present invention relates to an improved process for preparing R/S-γ-lipoic acid (6,8-dimercaptooctanoic acid) of the formula I or R/S-α-lipoic acid (D,L-thioctic acid) of the formula II

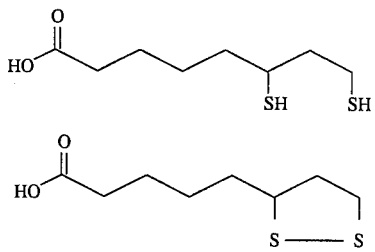

and to novel intermediates in this process.

R/S-α-Lipoic acid is a natural substance which occurs in low concentrations in virtually all animal and plant cells. It is a coenzyme in the oxidative decarboxylation of α-keto carboxylic acids (e.g. pyruvic acid) and is thus essential. This endogenous substance is used as racemate for the treatment of liver disorders and, increasingly, for the treatment of neuropathies (especially diabetic polyneuropathy). According to recent results (cf. CA 116(21): 2073606), α-lipoic acid may become important in the treatment of diseases caused by HIV-1 and HTLV IIIB viruses. In addition, γ-lipoic acid, which may be regarded as precursor of α-lipoic acid, has become increasingly important recently (cf. DE 40 35 456). There has thus been no lack of attempts to find an industrially advantageous process for preparing γ-lipoic acid and/or α-lipoic acid.

Thus, for example, the introduction to the description of DE 35 12 911 A1 describes a large number of multistage processes for preparing racemic α-lipoic acid, most of which are based on reaction of methyl adipoyl chloride with ethylene in the presence of aluminum chloride.

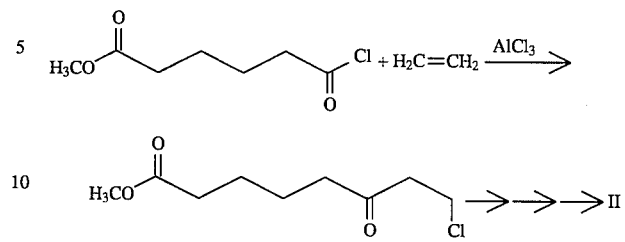

The chloro ketone formed in this way is converted by various processes in many stages into lipoic acid. The overall yield does not exceed 30%. The disadvantages of these processes are that they start from the relatively costly methyl adipoyl chloride and that a large number of steps are necessary and are very costly, some in terms of energy or of the reagents used.

The process claimed in DE 35 12 911 A1 for preparing γ-lipoic acid starting from 2-(3-alkylthiopropionyl)cyclopentanone by the reaction shown in the following diagram is also unsatisfactory.

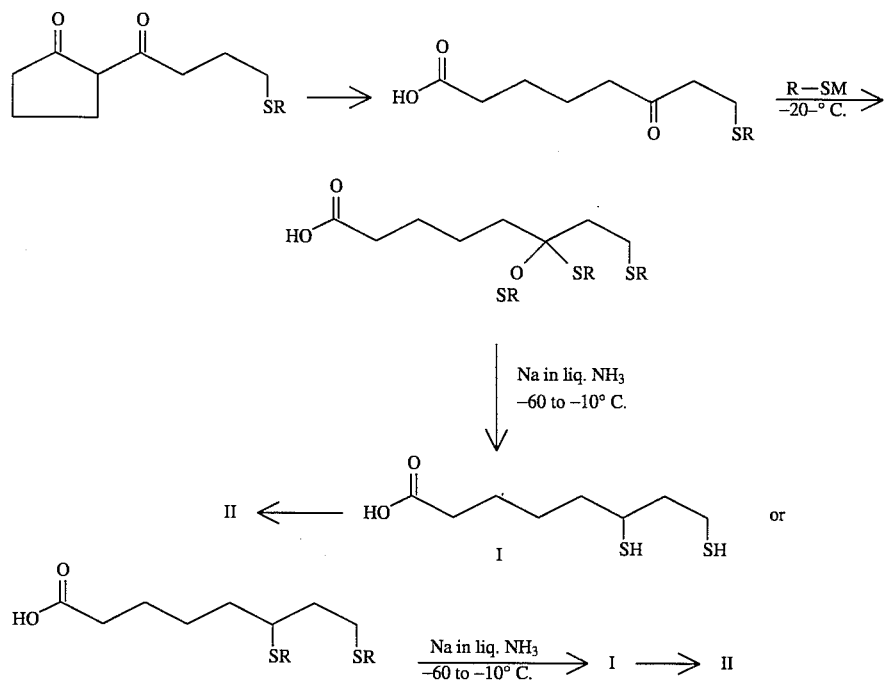

The disadvantages of this process are that the starting compounds are rather costly, because they have to be prepared in multistage processes, and the reaction with sodium in liquid ammonia at −60° to −10° C. is very costly too.

Furthermore, CA 63 (1965) 16355g discloses the preparation of α-lipoic acid from cyclohexanone as shown in the following scheme:

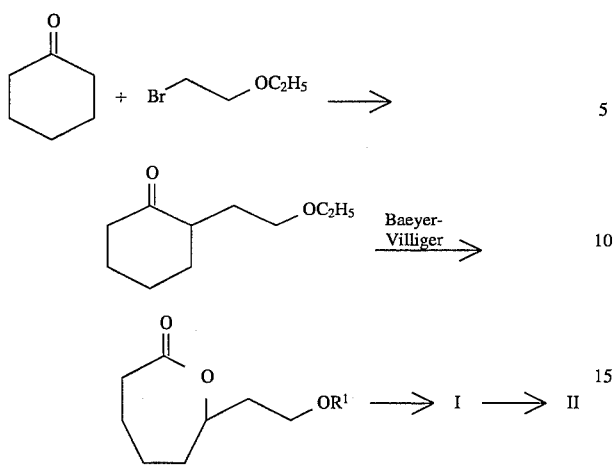

The disadvantages of this process are that the 2-ethoxyethyl bromide used as starting compound is very costly and that the overall yield of α-lipoic acid is only about 10%.

Overall yields of only about 19%, based on cyclohexanone, are obtained by the process disclosed in JACS 79 (1957) 3503–05 and U.S. Pat. No. 2,993,056 in the following way:

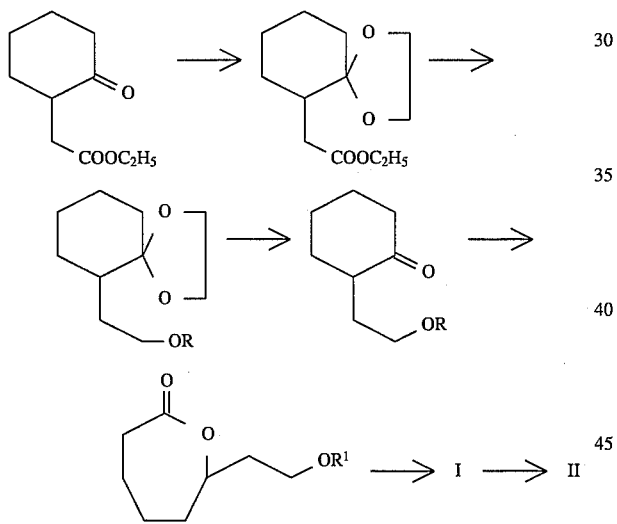

It is an object of the present invention to find a process for preparing R/S-α-lipoic acid with which it is possible to prepare this compound in good yields starting from a low-cost and easily obtainable starting material in a few steps which are easy to implement on the industrial scale. It is another object of the invention to find an advantageous synthetic route to R/S-γ-lipoic acid. We have found that this object is achieved by a process for preparing R/S-γ-lipoic acid (6,8-dimercaptooctanoic acid) of the formula I or R/S-α-lipoic acid of the formula II

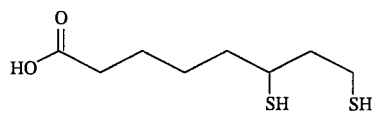

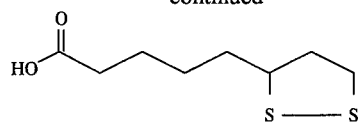

which comprises

A. reacting cyclohexanone in the presence of a suitable free radical initiator with a vinyl alkyl ether of the formula III

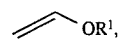

where $R^1$ is $C_1-C_3$-alkyl,

B. subjecting the resulting 2-alkoxyethylcyclohexanone of the formula IV

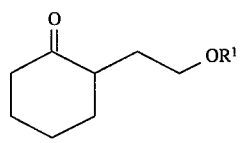

to a Baeyer-Villiger oxidation with an organic peracid or the salts thereof or an inorganic peroxo compound and C. reacting the resulting lactone of 8-alkoxy-6-hydroxyoctanoic acid of the formula V or the resulting mixture of this lactone and of 8-alkoxy-6-hydroxyoctanoic acid, formed by hydrolysis of this lactone, of the formula VI

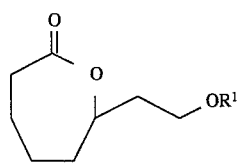

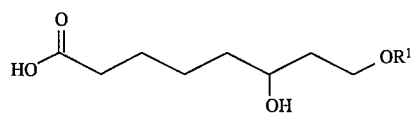

or the mixture which is obtained when performic acid is used and which is essentially composed of 8-alkoxy-6-formyloxyoctanoic acid of the formula VII

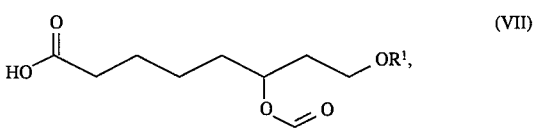

where $R^1$ is $C_1-C_3$-alkyl, together with small amounts of 8-alkoxy-6-hydroxyoctanoic acid of the formula VI and the lactone of the formula V, in a conventional manner in the presence of hydrobromic acid or hydriodic acid with thiourea to give R/S-γ-lipoic acid (6,8-dimercaptooctanoic acid) of the formula I, and isolating the latter, or D. converting the resulting crude R/S-γ-lipoic acid by aerial oxidation in the presence of catalytic amounts of iron(III) compounds into R/S-α-lipoic acid of the formula II, E. subjecting the resulting crude R/S-α-lipoic acid to a continuous distillation in a thin film evaporator under 0.02–0.2 mbar and at 60°–200° C., and F. crystallizing the resulting R/S-α-lipoic acid distillate.

The process according to the invention is particularly advantageous when the cyclohexanone is reacted in step A.

with the vinyl alkyl ether of the formula III, in particular with vinyl ethyl ether, in the presence of di-tert-butyl peroxide.

It is furthermore advantageous in the overall process to carry out the Baeyer-Villiger oxidation in step B. with sodium metaperborate or with permaleic acid prepared in situ from maleic anhydride and $H_2O_2$, the reaction of the lactone of 8-alkoxy-6-hydroxyoctanoic acid or the mixture of this lactone and 8-alkoxy-6-hydroxyoctanoic acid with thiourea in step C. in the presence of hydrobromic acid, and/or the conversion in step D. of the crude R/S-γ-lipoic acid by aerial oxidation into R/S-α-lipoic acid in the presence of iron(III) chloride, the distillation in step E. of the R/S-α-lipoic acid under from 0.05 to 0.1 mbar and at from 130° to 160° C. in a thin film evaporator, and the crystallization in step F. of the prepurified R/S-α-lipoic acid from diisopropyl ether or a mixture of hexane and ethyl acetate.

The process is very particularly advantageous when the Baeyer-Villiger oxidation in step B. is carried out with performic acid which is generated in situ from formic acid and hydrogen peroxide in the presence of 2-alkoxyethylcyclohexanone.

The process according to the invention provides a particularly advantageous synthetic route to R/S-γ-lipoic acid or R/S-α-lipoic acid starting from cyclohexanone and vinyl alkyl ethers, especially vinyl ethyl ether, which are easily obtainable and therefore very low-cost.

Thus, the yield of 2-alkoxyethylcyclohexanone from the free-radical addition of cyclohexanone onto vinyl ethyl ether in step A is about 70% after distillation.

Although free-radical addition of cyclohexanone onto vinyl ethers in yields of 50–65% has been described in Azerb. Khim. Zh., 3 (1980) 54–57, this was a purely academic study and was not connected with the preparation of lipoic acid. By contrast, the preparation of 2-ethoxyethylcyclohexanone from cyclohexanone and 2-ethoxyethyl chloride in a yield of only about 19% was described in JA-B 19939/65.

The free-radical addition of cyclohexanone onto vinyl acetate as described in C.R. Acad. Sc. Paris 289 (1979) 445–47 gave 2-acetoxyethylcyclohexanone in yields of only 20%, so that no advantageous synthetic route to α-lipoic acid starting from cyclohexanone appeared possible from this study either.

Cyclohexanone is used on a large scale as solvent and as starting material for polyamide syntheses and is therefore available at low cost and in large amounts.

The vinyl alkyl ethers which are also required as starting materials for the process according to the invention are prepared in a straightforward manner by addition of alcohols onto acetylene.

Re A. Suitable free-radical initiators for the addition of cyclohexanone onto vinyl alkyl ethers are dialkyl peroxides. Di-tert-butyl peroxide is particularly advantageous because it is particularly easily obtained and is therefore a low-cost commercial product, and it immediately forms free radicals at the boiling point of cyclohexanone. The general procedure for the reaction is to heat cyclohexanone to the boiling point and, while refluxing the cyclohexanone, slowly to add a solution of a free-radical initiator in the vinyl alkyl ether and, after the reaction is complete, to work up the mixture by distillation. From 5 to 20, preferably from 10 to 15, mol of cyclohexanone are used per mol of vinyl alkyl ether. The free-radical initiator is generally used in amounts of from 5 to 50 mol %, preferably 15–25 mol %, of the vinyl alkyl ether.

The reaction can be carried out in an inert solvent. However, it is particularly advantageous not to use additional solvent, ie. excess cyclohexanone acts as solvent.

The reactions generally take from 2 to 10, preferably 4 to 6, hours. The distillation of the reaction mixture takes place under reduced pressure.

Re B. The Baeyer-Villiger oxidation of alkoxyethylcyclohexanones to give lactones of the formula V or a mixture of these lactones with their hydrolysis products has been disclosed in C.A. 63 (1965) 16 355 g and JACS 79 (1957) 3503–05. The procedure for this oxidation is generally to react the 2-alkoxyethylcyclohexanone at from 0° to 150° C. (depending on the oxidizing agent) with an organic peracid or its salts or with an inorganic peroxo compound.

Suitable organic peracids are peracetic acid, perbenzoic acid, m-chloroperoxybenzoic acid, permaleic acid (prepared from maleic anhydride and 30% strength aqueous $H_2O_2$), perphthalic acid and its salts, especially magnesium salts, or inorganic peroxo compounds such as sodium metaperborate and percarbonate, which are commercially available in large amounts and at low cost. Whereas peracetic acid is mainly used in the prior art, preferably used in the process according to the invention is sodium metaperborate, ie. $NaBO_2.H_2O_2.3H_2O$, in acetic acid. The peracid or its salt is generally used in an amount of from 1 to 2, preferably 1.2 to 1.5, mol per mol of 2-alkoxyethylcyclohexanone. The reaction times depend on the temperature and are generally from 1.5 to 10, preferably 2 to 7, hours.

The mixture resulting from the reaction with sodium metaperborate contains not only the lactone of 8-alkoxy-6-hydroxyoctanoic acid of the formula V but also some of the free acid of the formula VI which is formed by hydrolysis of the lactone. Exclusively the lactone of the formula V is formed in anhydrous apolar solvents. The mixture resulting from the reaction is filtered to remove precipitated $NaH_2BO_3$ and is concentrated.

When sodium metaperborate is used, the overall yield of the mixture of the lactone of 8-alkoxy-6-hydroxyoctanoic acid and of the acid itself is about 90% of theory.

The peracid which has proven very particularly suitable for the Baeyer-Villiger oxidation is performic acid which is generated in situ from formic acid and hydrogen peroxide in the presence of the 2-alkoxyethylcyclohexanone of the formula IV.

This reaction results in a mixture of an 8-alkoxy-6-formyloxyoctanoic acid of the formula VII

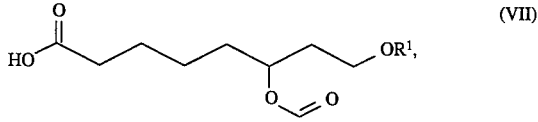

where $R^1$ is $C_1$–$C_3$-alkyl, together with small amounts of 8-alkoxy-6-hydroxyoctanoic acid of the formula VI and its lactone of the formula V in yields of 90–95% of theory.

8-Alkoxy-6-formyloxyoctanoic acids of the formula VII have not previously been described in the literature. They can be obtained in a purity of more than 98% from the mixture described above by continuous distillation under greatly reduced pressure, for example in a thin film evaporator. They can be converted in pure form, but also particularly advantageously in the form of the mixture described above, by reaction with thiourea in the presence of hydrobromic acid or hydroiodic acid (stage C) into R,S-γ-lipoic acid of the formula I which can be isolated or else converted according to the invention into R,S-α-lipoic acid, with the yield being 90–95% of theory.

In addition to the excellent yields, the use of performic acid also has great technical and ecological advantages. Thus, the two reactants employed in the Baeyer-Villiger oxidation with performic acid generated in situ, ie. in practice with formic acid and 30% aqueous hydrogen peroxide, are low-cost and safe to handle and, moreover, as liquids are considerably easier to meter by comparison with solid sodium metaperborate. Further advantages are that excess oxidizing agent can easily be decomposed thermally to $CO_2$ and $H_2O$ during work-up and that the 8-alkoxy-6-formyloxyoctanoic acids can be further processed immediately.

Although Baeyer-Villiger reactions with performic acid are known in principle (cf. Comprehensive Organic Synthesis, Ed. B. M. Trost, Pergamon Press 1991, Vol. 7, p. 671; C. Grudzinski et al., J. Chem. Soc. Perkin I (1978) 1182), all the described examples with cyclic ketones result in the corresponding lactones. Our finding that there is virtually quantitative formation of 8-alkoxy-6-formyloxyoctanoic acids is novel and unexpected.

It is likewise surprising that the 8-alkoxy-6-formyloxyoctanoic acids prepared according to the invention give on reaction with hydrogen bromide/thiourea R,S-γ-lipoic acid in yields of 90–95% of theory, whereas only 70–80% R,S-γ-lipoic acid is obtained starting from the lactone of 8-alkoxy-6-hydroxyoctanoic acid.

The Baeyer-Villiger oxidation with performic acid is generally carried out by dissolving the 2-alkoxyethylcyclohexanone of the formula IV in formic acid to give a 1–4 molar, preferably 1.5–2.5 molar, solution to which hydrogen peroxide in the form of a preferably 30% strength aqueous solution is then added in amounts of from 1.1 to 1.8, preferably 1.4 to 1.5, mol per mol of 2-alkoxyethylcyclohexanone.

The Baeyer-Villiger reaction according to the invention is preferably carried out at from 10° C. to 70° C., preferably from 40° to 50° C. The required temperature must be maintained by external cooling, especially at the start of the reaction. Products suitable for conversion to R,S-γ-lipoic acid are obtained by removing the formic acid/water mixture by distillation under atmospheric pressure. Pure 8-alkoxy-6-formyloxyoctanoic acid can be isolated from the crude product in a thin film evaporator.

Re C. The conversion of the lactone of the formula V or of the mixture of this lactone and 8-alkoxy-6-hydroxyoctanoic acid into R/S-γ-lipoic acid of the formula I is disclosed in JACS 79 (1957) 3503–05, and C.A. 63 (1965) 16355g, and is carried out in a conventional way. This entails the lactone or mixture of this lactone and 8-alkoxy-6-hydroxyoctanoic acid being mixed with about 8 mol of thiourea and about 7 mol of a concentrated hydrohalic acid and being refluxed for about 36 hours. Subsequently, a concentrated alkali metal hydroxide solution is added to the mixture, which is then refluxed with exclusion of air and light for about 12 hours to complete the hydrolysis.

It is subsequently acidified with HCl, and the R/S-γ-lipoic acid is extracted with a solvent which is of-low miscibility or immiscible with water. The R/S-γ-lipoic acid obtained by subsequent concentration can be either isolated as such or else oxidized to R/S-α-lipoic acid.

Re D. To prepare R/S-α-lipoic acid, the mixture obtained in step C. is oxidized with atmospheric oxygen in a weakly alkaline aqueous medium in the presence of iron(III) compounds. This oxidation is also disclosed in JACS 79 (1957), 3503–05, and is carried out in a conventional way. Iron(III) chloride is advantageously used as catalyst. The oxidation is carried out by passing atmospheric oxygen through the aqueous alkaline solution containing the iron(III) compound for the duration of the reaction. The reaction is generally carried out at from 15° to 40° C. and takes from 2 to 10 hours, depending on the aeration rate. Suitable iron(III) compounds are iron(III) halides, especially iron(III) chloride. They are generally used in catalytic amounts of from 0.1 to 0.5% of the weight of the R/S-γ-lipoic acid. The mixture after the oxidation is worked up by acidifying, extracting with a solvent which is of low miscibility or immiscible with water, and drying and concentrating the organic extract.

Re E. The resulting crude R/S-α-lipoic acid is continuously distilled according to the invention in a thin film evaporator, ie. an evaporator with a short holdup time, under greatly reduced pressure. The pressure is generally from 0.02 to 0.2, preferably 0.05 to 0.1 mbar, corresponding to temperatures from 60° to 200°, preferably 130° to 160° C., without decomposition.

Re F. The R/S-α-lipoic acid distillate obtained in this way can then be obtained in very pure form by crystallization from solvents such as diisopropyl ether or mixed solvents such as mixtures of n-hexane and ethyl acetate.

It is possible to obtain by the process according to the invention R/S-γ-lipoic acid and R/S-α-lipoic acid in very good yields in a relatively straightforward way starting from low-cost starting materials. Thus, R/S-α-lipoic acid is obtained in yields of about 45% based on vinyl alkyl ether.

EXAMPLE 1

1) Preparation of 2-(2-ethoxyethyl)cyclohexanone

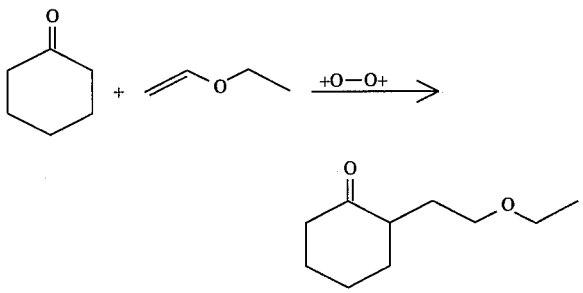

2940 g (30 mol) of cyclohexanone were heated to reflux while stirring and, at this temperature, a solution of 87.6 g (0.6 mol) of di-tert-butyl peroxide in 216 g (3 mol) of ethyl vinyl ether was added over the course of 5 hours (h). The mixture was subsequently refluxed for a further 1 h. After the mixture had cooled, the low boilers (tert-butanol, remaining vinyl ether and peroxide) and the excess cyclohexanone were removed by distillation under reduced pressure (25–40 mbar; diaphragm pump). The residue (about 500 g) was distilled under reduced pressure (0.5 to 2 mbar; oil pump). A total of 350 g of a 95% pure 2-(2-ethoxyethyl)cyclohexanone of boiling point 60°–65° C. (0.5 mbar) was obtained, corresponding to a yield of 69% of theory.

2) Preparation of the lactone of 8-alkoxy-6-hydroxyoctanoic acid

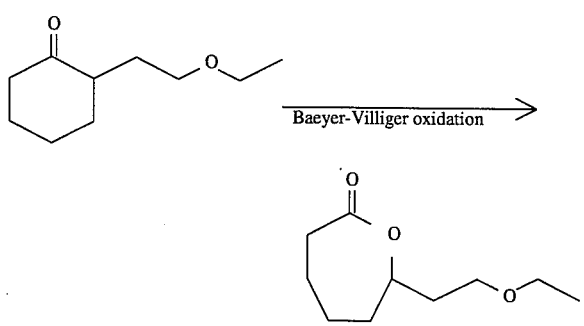

a) with 3-chloroperbenzoic acid as oxidizing agent 1506 g (4.8 mol) of 3-chloroperbenzoic acid (55% pure) were suspended in 2000 ml of CH$_2$Cl$_2$. 680 g (4 mol) of a 2-(2-ethoxyethyl)cyclohexanone prepared as in 1) were added dropwise to the suspension at a rate such that the vigorously stirred mixture did not boil too vigorously (about 2 h; highly exothermic reaction). The mixture was then stirred at 40° C. for 3 h. The mixture was cooled and then, while stirring vigorously, 3000 ml of a saturated Na$_2$CO$_3$ solution were slowly added. The phases were separated and the organic phase was washed with 2000 ml of Na$_2$CO$_3$ solution, dried over MgSO$_4$ and concentrated under reduced pressure to give 640 g of the lactone as a colorless liquid (95% according to analysis by gas chromatography (GC), corresponding to a yield of 86% of theory).

b) with sodium perborate as oxidizing agent 850 g (5 mol) of 2-(2-ethoxyethyl)cyclohexanone were dissolved in 3 l of acetic acid. The solution was heated to reflux and a suspension of 1150 g of NaBO$_2$.H$_2$O$_2$.3H$_2$O (7.5 mol) in 2 l of acetic acid was slowly added (exothermic reaction, evaporative cooling). The mixture was then refluxed for 1 h, cooled to 0° C. and filtered to remove precipitated sodium borate. The filtrate was concentrated at 70° C. under 30 mbar. The remaining crude product (mixture of 8-ethoxy-6-hydroxyoctanoic acid and its lactone) can be employed as such directly in the next stage.

3) Preparation of R/S-γ-lipoic acid (dihydrolipoic acid)

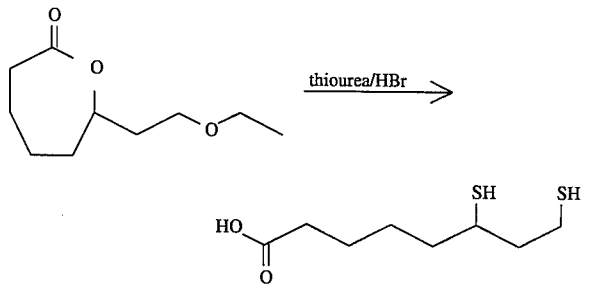

608 g (8 mol) of thiourea were dissolved in 1205 g (7 mol) of a 47% strength aqueous HBr, and 186 g (1 mol) of the lactone of 8-ethoxy-6-hydroxyoctanoic acid prepared as in 2a) were added to this. The mixture was then refluxed (105° C.) under protective gas for 36 h. Cooling to 50° C. resulted in a clear, pale yellow solution to which 3200 g (20 mol) of a 35% strength aqueous KOH were slowly added over the course of 1 h, and the resulting solution was refluxed in the dark for 10 h. A stream of nitrogen was passed through the reaction vessel during this time and during the subsequent acidification and was then passed through two wash towers (A: containing 4000 g of 20% strength HCl; B: containing a mixture of 3000 g of 10% strength NaOH and 3000 g of 10% strength NaOCl solution). After cooling, the reaction mixture was acidified (pH=1) with about 1100 g of concentrated HCl, and the crude R/S-γ-lipoic acid was removed by extraction three times with 1000 ml of methyl tert-butyl ether each time. Drying over MgSO$_4$ and concentration resulted in 210 g of crude R/S-γ-lipoic acid as a pale yellow oil containing 70–80% of α+γ-lipoic acid according to GC.

4) Preparation of R/S-α-lipoic acid

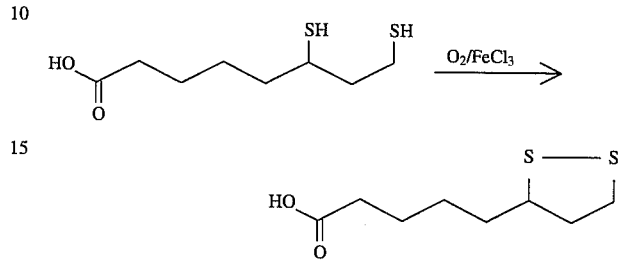

200 g of the crude R/S-γ-lipoic acid obtained as in 3) were dissolved in about 525 ml of 2N NaOH (pH=8–9). The mixture was diluted with 3600 ml of H$_2$O, and 4 ml of a 10% strength FeCl$_3$.6H$_2$O solution were added to the resulting solution. It was then passed through the deep red solution until the color changed to pale yellow (about 3 h). 1 of methyl tert-butyl ether was added and the pH was adjusted to about 1.5 with concentrated HCl. The phases were separated and then the aqueous phase was extracted twice more with 500 ml of methyl tert-butyl ether each time. The combined organic phases were dried and concentrated. The crude R/S-α-lipoic acid was distilled in a thin film evaporator at 150° C. under 0.1 mbar to give 160 g of yellow crystals. Two recrystallizations from diisopropyl ether provided 108 g of pure R/S-α-lipoic acid in the form of pale-colored crystals of melting point 61° C. GC content>99%, corresponding to a yield of 55.3% based on lactone of 8-ethoxy-6-hydroxyoctanoic acid.

EXAMPLE 2 a) Baeyer-Villiger oxidation with performic acid prepared in situ

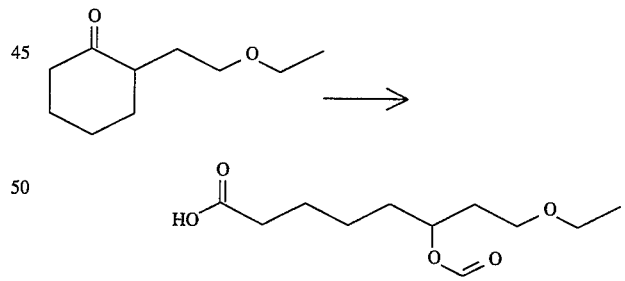

340 g (3 mol) of a 30% strength aqueous hydrogen peroxide were added to a solution of 340 g (2 mol) of 2-ethoxyethylcyclohexanone in 1 of formic acid over about 1 h, and the mixture was left to react for a further 1 h. The internal temperature was maintained at 45°±5° C. during this time.

The mixture was worked up by heating to 100° C. over the course of about 1 h, during which excess oxidizing agent decomposed with evolution of CO$_2$. Formic acid and water were then distilled out under slightly reduced pressure and at a bath temperature of about 100° C.

HPLC analysis of the residue showed that it contained 90–95% 8-ethoxy-6-formyloxyoctanoic acid together with small amounts of 8-ethoxy-6-hydroxyoctanoic acid, the corresponding lactone and a dimer.

8-Ethoxy-6-formyloxyoctanoic acid with a purity> 98% was obtained by continuous distillation of the crude product in a thin film evaporator at 130° C. under 0.05 mbar.

b) Preparation of R,S-γ-lipoic acid

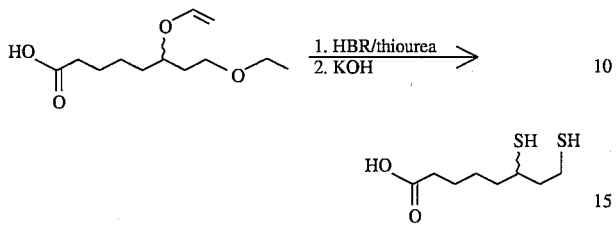

608 g (8 mol) of thiourea were dissolved in 1205 g (7 mol) of a 47% strength aqueous hydrobromic acid. To this were added 242 g (about 1 mol) of the crude 8-ethoxy-6-formyloxyoctanoic acid prepared as in Example 2a, and the mixture was refluxed for 36 h.

The clear pale yellow solution of the thiuronium salts was run over the course of 1 h into 3200 g (20 mol) of a 35% strength aqueous potassium hydroxide solution under inert gas with exclusion of light, and the mixture was refluxed for 8 h. During this time and during the subsequent acidification, a stream of inert gas was passed through the reaction vessel and then to two wash towers (W). WI contained 4000 g of a 20% strength hydrochloric acid, and WII contained a mixture of 3000 g of a 10% strength sodium hydroxide solution and 3000 g of a 10% strength sodium hypochloride solution.

The reaction mixture was cooled to 25° C. and then acidified to pH 1–2 with about 1100 g of concentrated hydrochloric acid, and the R,S-γ-lipoic acid was removed by extraction three times with 1000 ml of methyl tert-butyl ether each time. Concentration resulted in 218 g of crude product R,S-γ-lipoic acid as a pale yellow oil which was suitable for conversion into R,S-α-lipoic acid.

The product was subjected to continuous distillation in a thin film evaporator (150° C., 0.1 mbar) to remove solvent residues and involatile components. Analysis by GC and HPLC showed that the distillate (195 g) comprises a 9/1 mixture of R,S-γ-lipoic acid and R,S-α-lipoic acid; this corresponds to an overall yield of required product of 93.7% of theory.

We claim:

1. A process for preparing R/S-γ-lipoic acid (6,8-dimercaptooctanoic acid) of the formula I or R/S-α-lipoic acid of the formula II

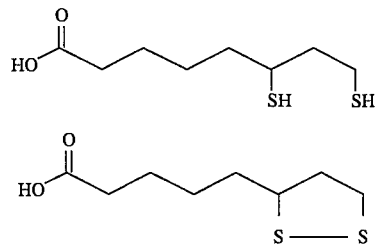

which comprises

A. reacting cyclohexanone in the presence of a suitable free radical initiator with a vinyl alkyl ether of the formula III

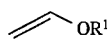

where $R^1$ is $C_1$–$C_3$-alkyl,

B. converting the resulting 2-alkoxyethylcyclohexanone of the formula IV

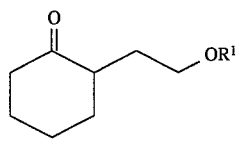

by Baeyer-Villiger oxidation with performic acid prepared in situ into a mixture of 8-alkoxy-6-formyloxyoctanoic acid of the formula VII

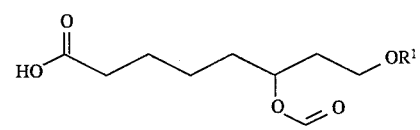

where $R^1$ is $C_1$–$C_3$-alkyl, and small amounts of 8-alkoxy-6-hydroxyoctanoic acid of the formula VI and its lactone of the formula V

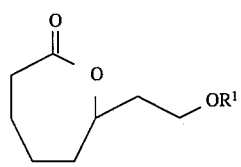

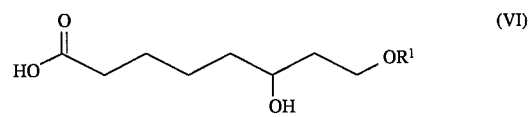

C. reacting the resulting mixture in a conventional manner in the presence of hydrobromic acid or hydriodic acid with thiourea to give R/S-γ-lipoic acid (6,8-dimercaptooctanoic acid) of the formula I, and isolating the latter, or D. converting the resulting crude R/S-γ-lipoic acid by aerial oxidation in the presence of catalytic amounts of iron(III) compounds into R/S-α-lipoic acid of the formula II, E. subjecting the resulting crude R/S-α-lipoic acid to a continuous distillation in a thin film evaporator under 0.02 to 0.2 mbar and at 60°–200° C., and F. crystallizing the resulting R/S-α-lipoic acid distillate.

2. The process of claim 1 wherein the performic acid is in the form of a 1–4 molar solution in formic acid with hydrogen peroxide.

3. A process for preparing R/S-γ-lipoic acid (6,8-dimercaptooctanoic acid) of the formula I or R/S-α-lipoic acid of the formula II

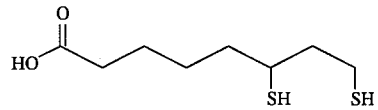

-continued

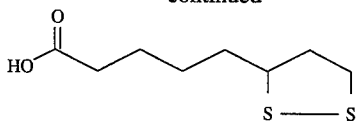  (II)

which comprises

A. reacting cyclohexanone in the presence of ditert-butyl peroxide with a vinyl alkyl ether of the formula III

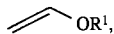  (III)

where $R^1$ is $C_1$–$C_3$-alkyl,

B. converting the resulting 2-alkoxyethylcyclohexanone of the formula IV

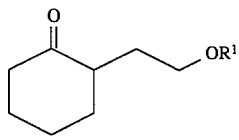  (IV)

by Baeyer-Villiger oxidation with performic acid prepared in situ into a mixture of 8-alkoxy-6-formyloxyoctanoic acid of the formula VII

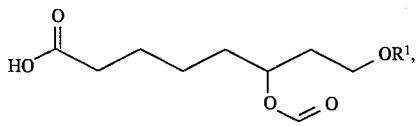  (VII)

where $R^1$ is $C_1$–$C_3$-alkyl, and small amounts of 8-alkoxy-6-hydroxyoctanoic acid of the formula VI and its lactone of the formula V

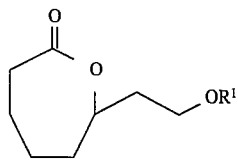  (V)

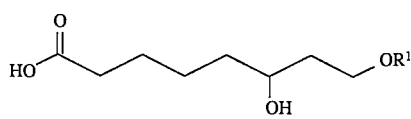  (VI)

C. reacting the resulting mixture in a conventional manner in the presence of concentrated hydrobromic acid with thiourea to give R/S-γ-lipoic acid (6,8-dimercaptooctanoic acid) of the formula I, and isolating the latter, or D. converting the resulting crude R/S-γ-lipoic acid by aerial oxidation in the presence of catalytic amounts of iron(III) chloride into R/S-α-lipoic acid of the formula II, E. subjecting the resulting crude R/S-α-lipoic acid to a continuous distillation in a thin film evaporator under from 0.05 to 0.1 mbar and at a temperature of from 130° to 160° C., and F. crystallizing the resulting R/S-α-lipoic acid distillate from diisopropyl ether or a mixture of hexane and ethyl acetate.

* * * * *